United States Patent

Cowman et al.

[11] Patent Number: 5,873,913
[45] Date of Patent: Feb. 23, 1999

[54] OPTICAL BRIGHTENING AGENTS

[75] Inventors: John Stuart Cowman, Bradford; John Martin Farrar, Leeds; Mark David Graham, Leeds; Neil Mackinnon, Leeds, all of Great Britain

[73] Assignee: Clariant Finance (BVI) Limited, Tortola, United Kingdom

[21] Appl. No.: 765,468

[22] PCT Filed: Jun. 22, 1995

[86] PCT No.: PCT/EP95/02433

§ 371 Date: May 7, 1997

§ 102(e) Date: May 7, 1997

[87] PCT Pub. No.: WO96/00221

PCT Pub. Date: Jan. 4, 1996

[30] Foreign Application Priority Data

Jun. 23, 1994 [GB] United Kingdom ............... 9412590

[51] Int. Cl.$^6$ .............. C07D 251/70; C07D 403/14; D06L 3/00
[52] U.S. Cl. .................. 8/648; 162/162; 442/130; 510/394; 544/193.2
[58] Field of Search .......................... 544/193.2

[56] References Cited

U.S. PATENT DOCUMENTS

| | | | |
|---|---|---|---|
| 3,871,898 | 3/1975 | Reinhert et al. | 117/33.5 T |
| 3,979,285 | 9/1976 | Wegmuller et al. | 210/36 |
| 4,025,507 | 5/1977 | Fleck et al. | 544/193.2 |
| 4,115,124 | 9/1978 | Hamilton et al. | 96/82 |
| 4,200,489 | 4/1980 | Tlach et al. | 162/162 |
| 4,271,395 | 6/1981 | Brinkmann et al. | 331/94.5 |
| 4,339,238 | 7/1982 | Fringeli et al. | 8/527 |
| 4,364,845 | 12/1982 | Fringeli | 252/301.22 |
| 4,374,643 | 2/1983 | Suzuki et al. | 8/648 |
| 4,444,871 | 4/1984 | Miyaoka et al. | 430/378 |
| 4,587,195 | 5/1986 | Ishikawa et al. | 430/139 |
| 4,605,511 | 8/1986 | Fringeli | 252/301.21 |
| 4,861,344 | 8/1989 | Schlafer et al. | 8/532 |
| 4,880,726 | 11/1989 | Shiba et al. | 430/376 |
| 4,898,933 | 2/1990 | Schlafer et al. | 534/605 |
| 5,051,111 | 9/1991 | Anceschi et al. | 8/648 |
| 5,238,793 | 8/1993 | Hoyen, Jr. | 430/446 |
| 5,591,257 | 1/1997 | Weide et al. | 106/496 |
| 5,656,760 | 8/1997 | Bacher et al. | 544/193.2 |

FOREIGN PATENT DOCUMENTS

| | | |
|---|---|---|
| 817 127 | 2/1975 | Belgium . |
| 0 376 893 | 7/1990 | European Pat. Off. . |
| 2067301 | 8/1991 | France . |
| 62-106965 | 5/1917 | Japan . |
| 50-29885 | 3/1975 | Japan . |
| 51-36832 | 10/1976 | Japan . |
| 60-158266 | 8/1985 | Japan . |
| 63-282382 | 11/1988 | Japan . |

OTHER PUBLICATIONS

Official Gazette, 1134 OG 198, 98 and 99, Jan. 7, 1992.
Derwent Publication abstract of J5 029–885 Mar. 25, 1975.
Derwent Publication abstract J6 1058–266–A Aug. 19, 1985.
Derwent Publication abstract of J6 2106–965–A May 18, 1987.
Derwent Publication abstract of J6 3282–382–A Nov. 18, 1988.
Derwent Publication abstract of J7 6036–832 Oct. 12, 1976.

*Primary Examiner*—Mukund J. Shah
*Assistant Examiner*—Bruck Kifle
*Attorney, Agent, or Firm*—Scott E. Hanf

[57] ABSTRACT

Optical brightening agents for use in textiles, paper, detergents correspond to the formula

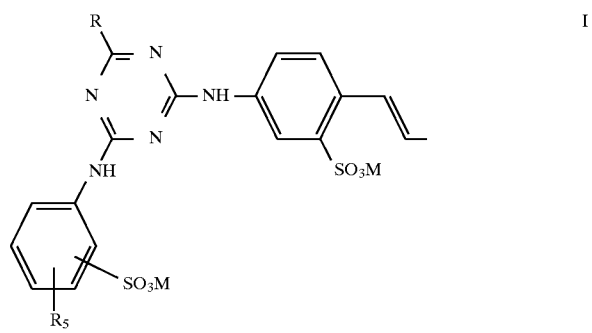

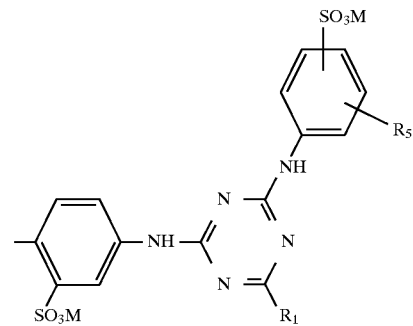

where R, $R_1$ are preferably derived from amino-acids, particularly glutamic and iminodiacetic acids.

6 Claims, 2 Drawing Sheets

OPTICAL BRIGHTENING AGENTS

This invention relates to novel organic compounds based on 4,4'-diaminostilbene-2,2'-disulphonic acid.

4,4'-diaminostilbene-2,2'-disulphonic acid., known generally as "DAS", is the starting material for a number of important products used in industry, most importantly various dyestuffs and optical brighteners. DAS-based optical brighteners (OBAs) find a wide range of uses in detergents, paper, textiles and so on.

One of the standard ways of making an optical brightener is to substitute the amino groups of DAS with substituted triazines. This may be done, for example, by reacting DAS with cyanuric chloride and then further reacting the remaining chlorines on the cyanuric chloride moiety. A popular substitutent for one of these chlorines is provided by sulphanilic acid.

It has now been found that it is possible to make a new class of DAS-based compounds whose performance is substantially better than that of known sulphanilic acid-based materials. The invention therefore provides a compound in free acid or salt form of the formula I

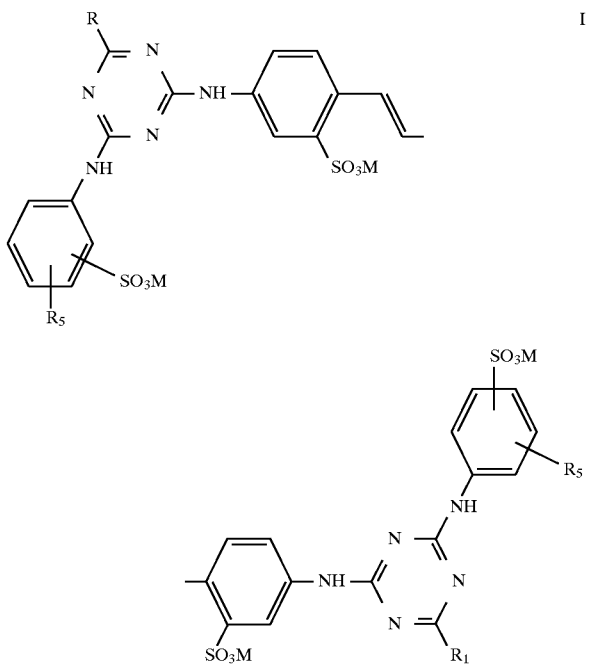

wherein

R, $R_1$ are moieties which are the same or different and have the formula $-NR_2R_3$, wherein:
(a) $R_2$ is selected from
  (i) hydrogen;
  (ii) $C_{1-6}$ alkyl, optionally substituted with at least one of mercapto, $C_{1-6}$ thioalkyl, OH and $SO_3M$; and
  (iii) $-R_4(CO_2M)_x$
    wherein $R_4$ is an aliphatic moiety having from 1–6 carbon atoms, those valencies not bonded with groups $CO_2M$ being bonded with at least one of H, mercapto, $C_{1-6}$ thioalkyl, OH and $SO_3M$, x is an integer of from 1–4 and M is selected from hydrogen, a colourless cation or an amine-derived cation;
  with the proviso that, when $R_2$ is selected only from (i) or (ii), any group (ii) is substituted with at least both of OH and $SO_3M$;
(b) $R_3$ is selected from groups $R_2$, hydrogen and $C_{3-6}$ alkyl, with the provisos that $R_2$ and $R_3$ cannot both be hydrogen, and when one of $R_2$, $R_3$ is hydrogen, the other cannot be $-(NHCH_2CO_2H)$;
or $R_2$ and $R_3$ together with the nitrogen atom form a ring having from 5–6 members only one of which is heterocyclic, which ring is singly substituted with $-COOM$ or $-SO_3M$;
and $R_5$ are selected independently from the group consisting of hydrogen, methyl, $C_{1-6}$alkoxy and halogen.

In a preferred embodiment of the invention, $R_5$ is hydrogen and the sulphonic acid groups on the phenylene rings attached to the triazine rings are meta or para to the connecting amino groups, that is, the particular moieties attached to the triazine rings are derived from sulphanilic acid or metanilic acid.

The moieties R and $R_1$ may be derived from any suitable compounds known to the art. It is preferred that they be amino-acid residues. Examples of suitable acids include glycine, aspartic acid, serine, hydroxy glutamic acid and alanine, but the preferred acids are glutamic acid and iminodiacetic acid.

The most preferred compounds are those derived from metanilic acid or sulphanilic acid and where R is derived from glutamic or iminodiacetic acid.

In the case where $R_2$ and $R_3$ together with the nitrogen atom of groups R, $R_1$ form a ring, it is preferred that this ring be a pyrollidine ring substituted with $-COOM$.

The compounds according to the invention may be prepared in free acid form or in salt form such as with an alkali metal cation, an organic amine salt, a mixed or partial salt.

The materials M are preferably either metal cations, particularly sodium and potassium, or simple alkanolamines such as mono-, di-and triethanolamine.

Two of the most preferred compounds have the formulae II and III

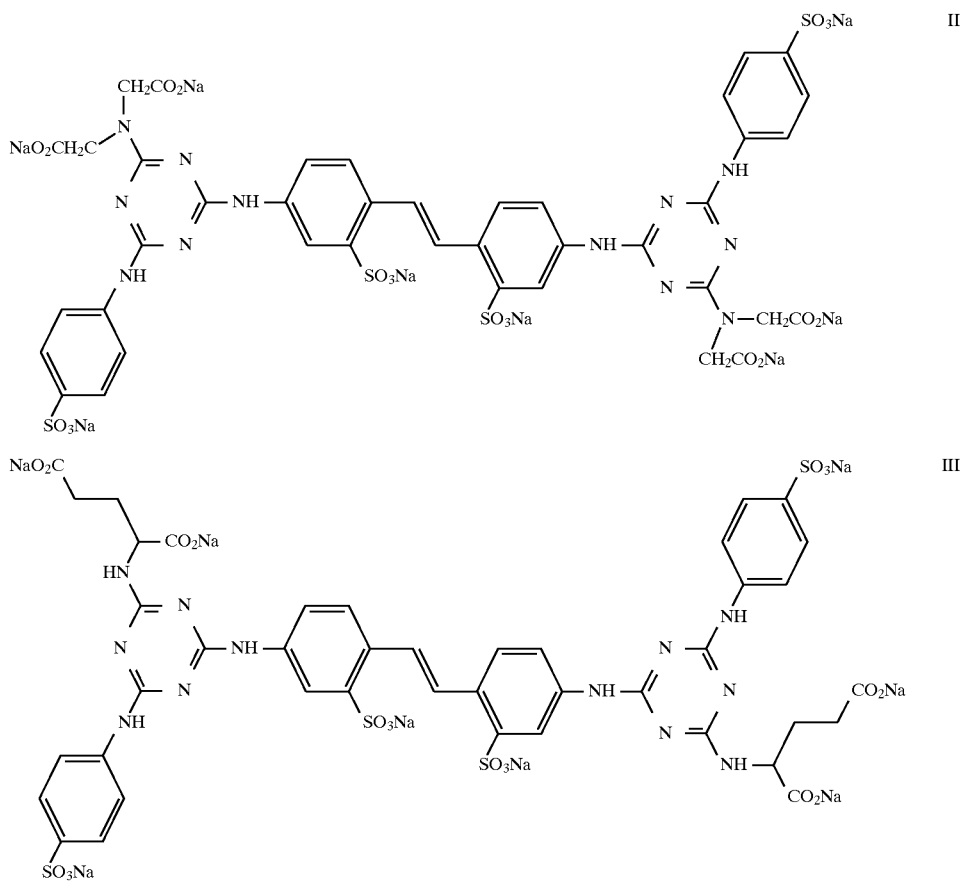
Other compounds which also perform well are those which have the formulae IV–XI
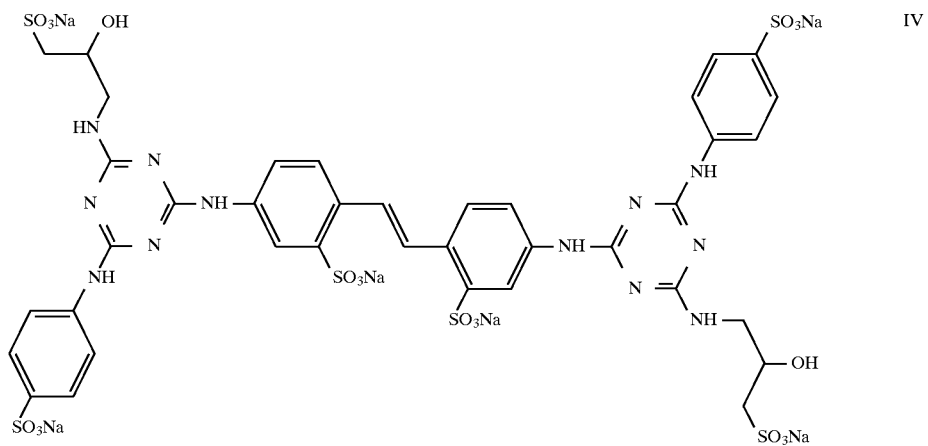

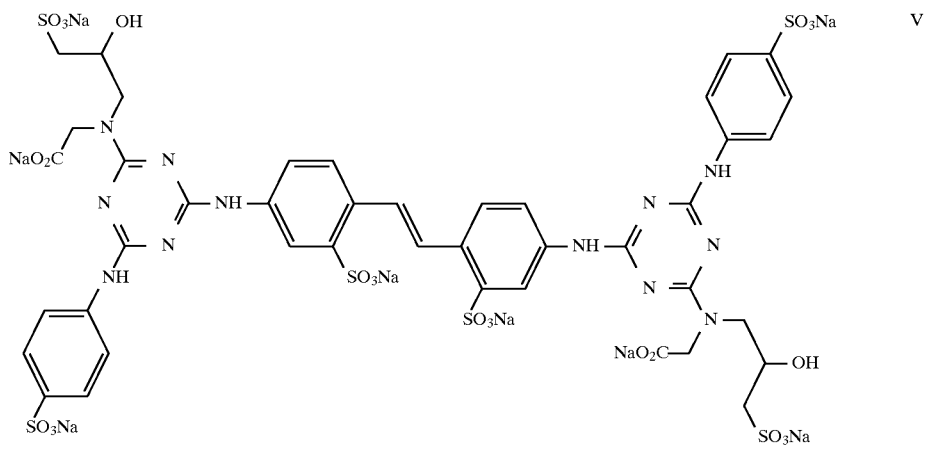
V
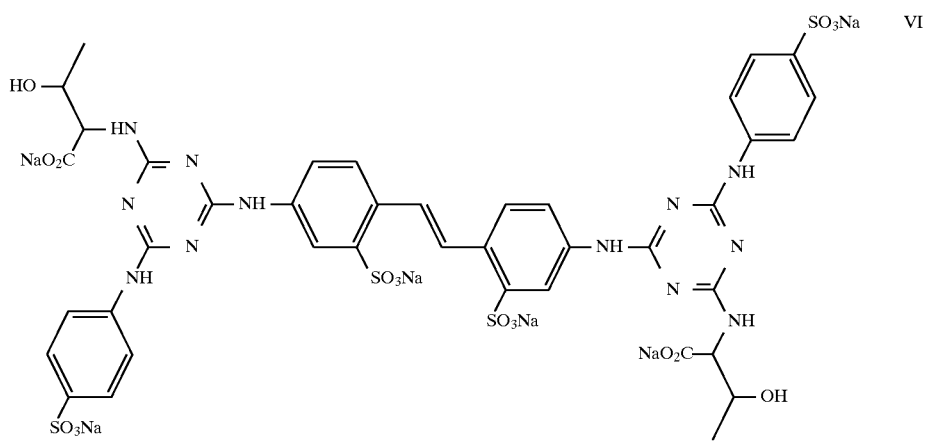
VI
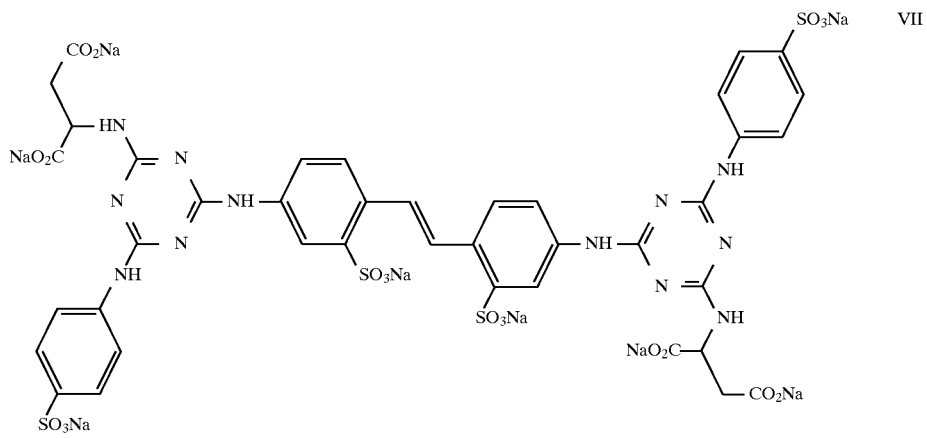
VII

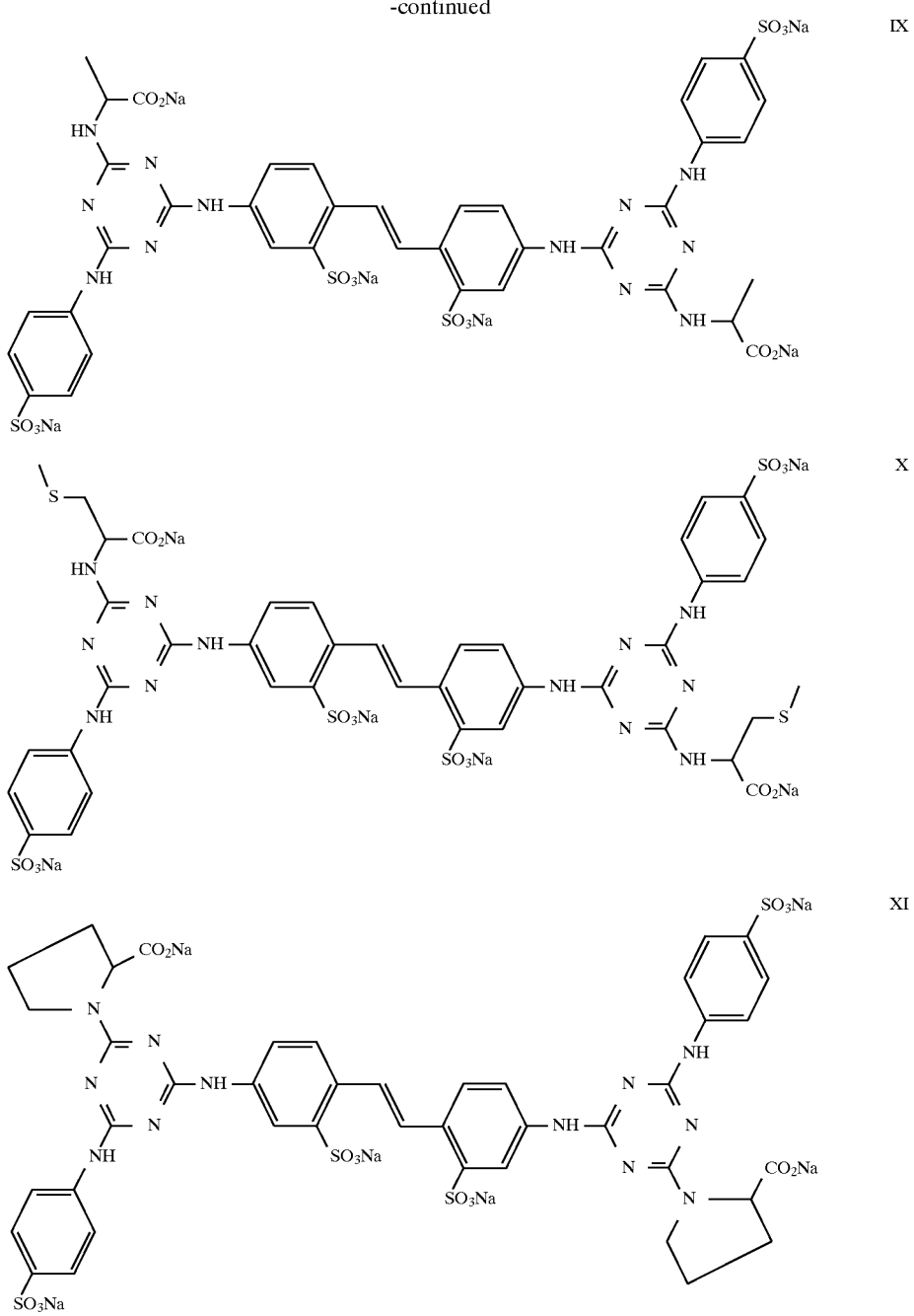

The compounds according to this invention may be prepared by standard synthetic methods using readily-obtainable reagents.

The compounds may be used individually or in admixture. It has been found that some of them, particularly the aminodiacetic acid/glutamic acid -sulphanilic acid-derived material referred to hereinabove, exhibit outstanding optical brightening characteristics. The compounds according to the invention are therefore very useful as optical brightening agents (OBAs) in paper, textiles and so on.

The compounds of the invention are particularly effective when used as optical brightening agents for paper. They may be applied to paper either by addition to a paper stock prior to sheet formation or -they may be incorporated into a coating composition which is subsequently applied to a paper sheet. Incorporation into a size which is then used on paper is particularly effective. The compounds may also be applied to the surface of the paper in conjunction with certain additives which are well known to boost the performance of the optical brightening agents, such as: carboxymethyl cellulose, polyethylene glycols, alkanolamines, polyvinyl alcohols etc.

The invention therefore provides a process for making paper comprising the addition of a compound of formula I to a paper stock.

Furthermore, the invention provides a process for making paper comprising the addition of a compound of formula I to a paper coating composition.

Still further the invention provides a process for treating textiles comprising the addition of a compound of formula I thereto.

The invention also provides paper comprising a compound of formula I and furthermore textiles comprising a compound of formula I.

Still further the invention provides the use of a compound of formula I as an optical brightener for detergents, paper or textiles, preferably in coating methods after paper sheet formation.

The invention is further described by reference to the following non-limiting examples, in which all parts are expressed by weight.

PREPARATION EXAMPLE

Figure 1:
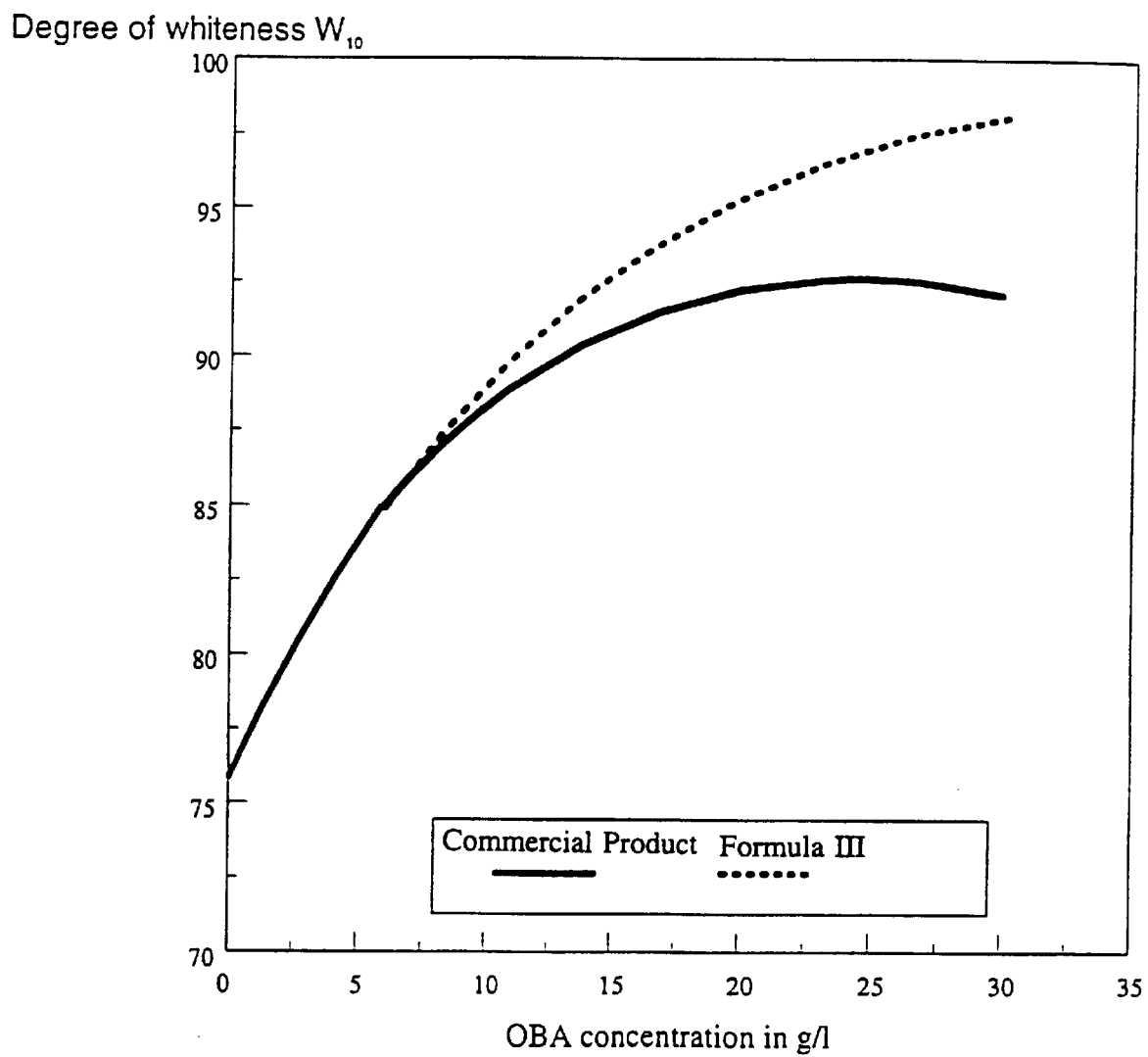
FIG. 1 is a graph charting whiteness against optical brightening agent concentrations in g/l.

Preparation of a compound according to Formula III.

Stage 1

A solution of 18.4 parts of cyanuric chloride in 100 parts of acetone is allowed to run into a mixture of 300 parts of crushed ice and 500 parts of water, while cooling. A solution of 20.7 parts of the sodium salt of 4,4'-diamino-2,2' stilbenedisulphonic acid in 150 parts of water is then introduced dropwise into this mixture at a temperature in the range of 0° to 5° C. and the reaction mixture is kept weakly acid to Congo paper by adding sodium bicarbonate. Stirring is continued at 0° to 5° C. until no primary aromatic amine group is detectable by diazotization.

Stage 2

A solution of 19.6 parts of sulphanilic acid sodium salt in 200 parts of water is added slowly to the reaction mixture from Stage 1, keeping the temperature at 5° to 10° C. and the pH at neutral by simultaneous addition of dilute sodium hydroxide solution. When the addition is complete, the mixture is heated to 50° C. and stirring is continued until no primary aromatic groups can be detected by diazitization.

Stage 3

15 parts of glutamic acid is added to the reaction mixture from Stage 2 and the mixture is heated to reflux. The pH is kept at 8 by addition of dilute sodium hydroxide solution during this process. The acetone is allowed to distil off and the mixture is refluxed for 5 hours. The reaction mixture is concentrated and salt is added to precipitate the product. The product is filtered off and washed with 10% brine.

Application Example 1

10 parts of the compound of formula III is dissolved in 50 parts of distilled water. 100 parts of a typical size-press starch is made up in 1000 parts of water and cooked at 90° C.

It is then cooled to 60° C. The brightener solution is then incorporated into the starch solution. A paper base or board is surface coated with the starch/brightener solution in the size-press or film-press and dried at 80°–120° C. in the drying section of the paper machine.

A paper or board with a considerably improved degree of whiteness is thus obtained.

Application Example 2

An aqueous solution of the compound of formula III is dosed under stirring into a warm (60° C.) solution of an anionic oxidised potato starch ("Perfectamyl" (trade mark) A4692), together with water to give a starch solution of 5% and a known amount of compound.

The brightened starch solution is then poured between the moving rollers of a laboratory size-press (forming a pond) and a paper base sheet (a commercial white paper 75 g/m$^2$, neutral sized, CIE Whiteness 72, without a size-press coating) is then passed between the rollers, through the solution. The paper coated with the wet starch solution is then dried for 5 minutes at 70° C. in a flat bed drier.

The paper is weighed before application and whilst wet to determine the pick-up of wet starch solution and therefore the pick-up of starch.

Once dried, the paper sheets are allowed to condition, and the CIE Whiteness ($W_{10}$) of each sheet is then calculated from measurements made on a calibrated spectrophotometer.

The process is repeated with an equal amount of a commercially-available OBA ("Leucophor" (trade mark) U) substituted for the compound according to the invention.

The resulting CIE Whiteness values for the compound and the commercial product on the paper are shown in the graph of FIG. 1. The degree of Whiteness $W_{10}$ is calculated from the formula (from ISO 105–502).

$$W_{10}=Y_{10}+800(0.3138-x_{10})+1700(0.3310-y_{10})$$

The superior performance of the compound according to the invention is noticeable from low proportions of compound

Application Example 3

An aqueous solution of a compound of formula III is dosed under stirring, into a coating composition (described below) together with water to give a constant solids content and a known amount of the compound. The brightened coating composition solution is then coated on to a suitable base paper using an automatic wire-wound bar applicator with a standard speed setting and a standard load on the bar. The paper coated with the solution is then dried in a hot air flow for 5 minutes. A known area of the paper is weighed before application and after drying to determine the coating weight applied.

Once dried, the paper sheets are allowed to condition, and the CIE Whiteness ($W_{10}$) of each sheet is calculated from measurements made on the same calibrated spectrophotometer.

The coating composition recipe is:

| | |
|---|---|
| Pigment:-China Clay SPS | 100 parts |
| Water | 64.4 parts |
| Dispersing agent[1] | 0.6 parts |
| Latex[2] | 20 parts |
| 20% Starch solution[3] | 25 parts |
| Solids content approx. = 55% | |

[1]. "Polysalz" (trade mark), a sodium salt of a polyacrylic acid, is used
[2]. "Acronal" (trade mark) S320D, an acrylic ester copolymer, is used
[3]. "Perfectamyl" A4692

Figure 2:
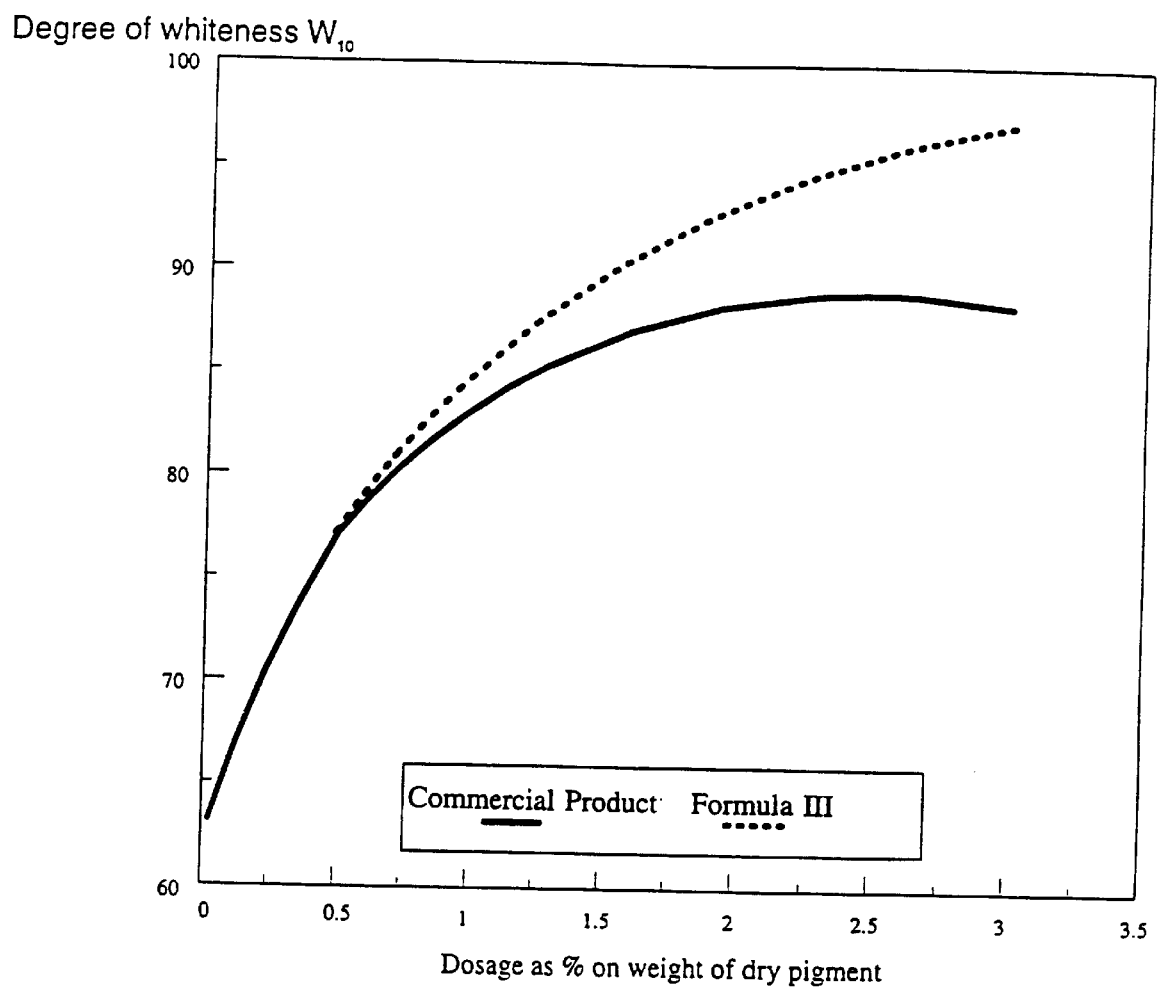
FIG. 2 is a graph charting whiteness against optical brightening agent dosage as a % of dry pigment.

The experiment is repeated using the same quantity of a commercially-available optical brightening agent. The results are shown in the graph of FIG. 2. Again, it can be seen that the compound of the present invention performs significantly better than that of the commercial optical brightening agent.

We claim:
1. A compound in free acid or salt form of the formula I

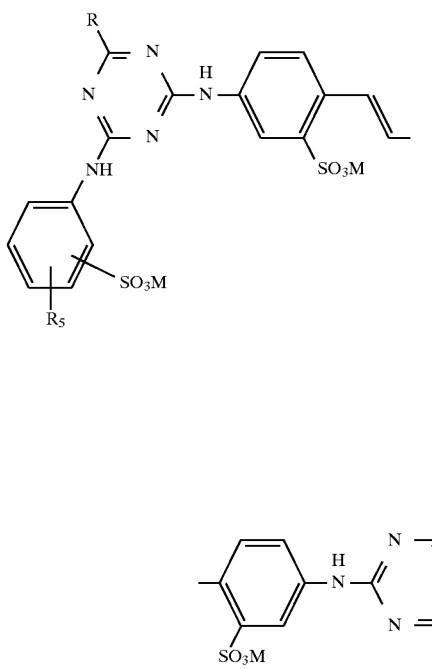

wherein
R, $R_1$ are moieties which are the same or different and have the formula —$NR_2R_3$,
wherein:
(a) $R_2$ is selected from
(i) hydrogen;
(ii) $C_{1-6}$ alkyl, optionally substituted with at least one of mercapto, $C_{1-6}$ alkylthio, OH and $SO_3M$; and
(iii) —$R_4(CO_2M)_x$
wherein $R_4$ is an aliphatic moiety having from 1–6 carbon atoms, those valences not bonded with groups $CO_2M$ being bonded with at least one of H, mercapto, $C_{1-6}$ alkylthio, OH and $SO_3M$, x is an integer of from 1–4 and M is selected from hydrogen, or a colourless cation;
with the provisos that, when $R_2$ is selected only from (i) or (ii), any group
(ii) is substituted with at least both of OH and $SO_3M$;
(b) $R_3$ is as defined in $R_2$ with the proviso that $R_2$ and $R_3$ cannot both be hydrogen, and when one of $R_2$, $R_3$ is hydrogen, the other cannot be —($CH_2CO_2H$);
or $R_2$ and $R_3$ together with the nitrogen atom form a pyrrolidine ring, said ring is singly substituted with —COOM or —$SO_3M$;
and $R_5$ is selected from the group consisting of hydrogen, methyl, $C_{1-6}$ alkoxy and halogen.

2. A compound according to claim 1, wherein $R_5$ is hydrogen and the $SO_3M$ groups on the phenylene rings attached to the triazine rings are meta or para to the connecting amino groups.

3. A compound according to claim 1, wherein R, $R_1$ are residues of amino-acids.

4. A compound according to claim 3, wherein the amino-acids are selected from the group consisting of glycine, aspartic acid, serine, hydroxyglutamic acids, alanine, glutamic acid and iminodiacetic acid.

5. A compound according to claim 1, having a formulae selected from the group consisting of the formulae II and III.

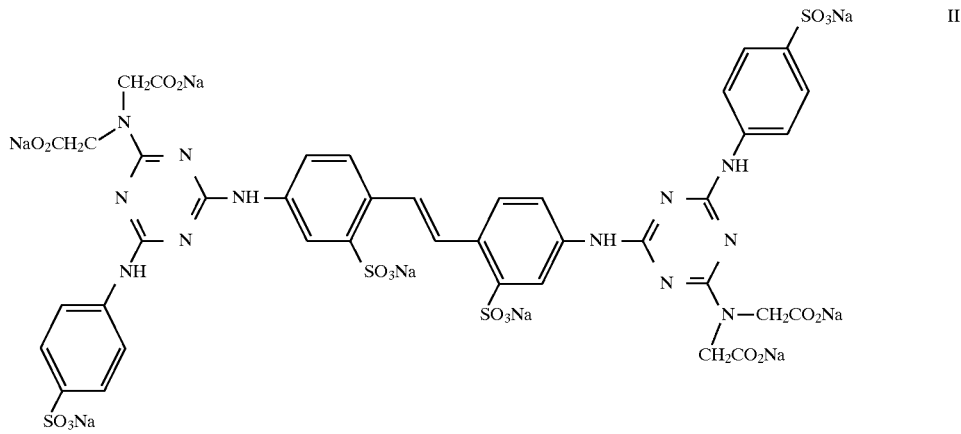

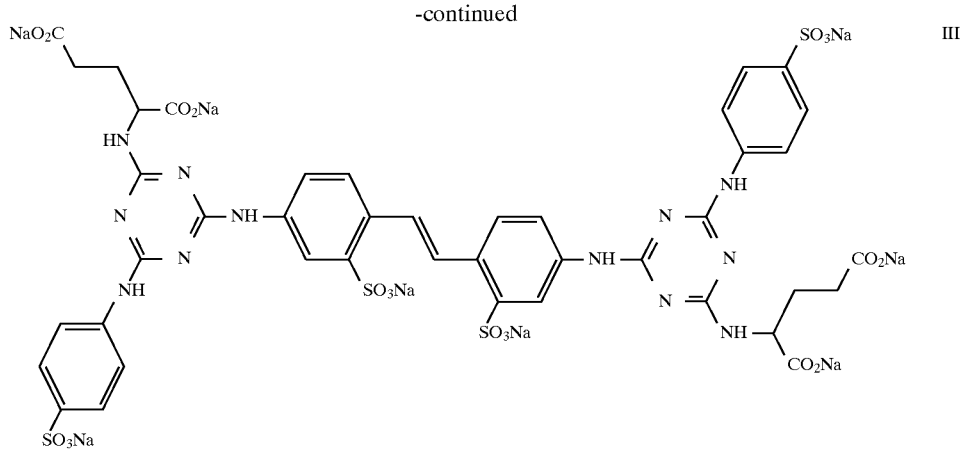
6. A method of producing an optically brightened paper or textiles, or an optical brightener containing detergent comprising the step of adding the compound of formula I, as claimed in claim 1, to a member selected from the group consisting of detergents, paper, paper stock, paper coatings and textiles.
* * * * *